United States Patent [19]

Bell

[11] Patent Number: 4,516,976
[45] Date of Patent: May 14, 1985

[54] ADHESIVE TAPE FASTENERS

[75] Inventor: John E. Bell, Columbia, S.C.

[73] Assignee: Anchor Continental Inc., Columbia, S.C.

[21] Appl. No.: 504,026

[22] Filed: Jun. 13, 1983

[51] Int. Cl.³ ............................................. A41B 13/02
[52] U.S. Cl. .................................................... 604/389
[58] Field of Search ........................ 604/374, 389, 390

[56] References Cited

U.S. PATENT DOCUMENTS

| | | |
|---|---|---|
| 3,848,594 | 11/1974 | Bnell . |
| 3,951,149 | 4/1976 | Ness .................................... 604/390 |
| 3,999,546 | 12/1976 | Feldman et al. . |
| 4,020,842 | 5/1977 | Richman ............................ 604/390 |

Primary Examiner—Stephen C. Pellegrino
Assistant Examiner—Christa K. Scott
Attorney, Agent, or Firm—F. R. Brockington

[57] ABSTRACT

An adhesive tape fastener for a diaper, which has a front surface and a back surface, which fastener comprises a first, second and third adhesive tape each of which has its front face coated with a pressure sensitive adhesive. The first adhesive tape has a free end portion which is adapted for attachment to a marginal portion of the front surface of the diaper and a fixed end which is joined to the adhesive face of a second adhesive tape. The second adhesive tape has a free end portion which is adapted to form a first fastening tab and a fixed end which is joined to the adhesive face of a third adhesive tape. The third adhesive tape has a first free portion which is adapted to form a second fastening tab and a second free end portion which is adapted for attachment to a marginal portion of the back surface of the diaper to form a second anchor tab. The second anchor tab is finger tearable whereby in use it can be detached from the fastener to allow the first fastening tab to be used to refasten the diaper.

8 Claims, 4 Drawing Figures

ADHESIVE TAPE FASTENERS

The invention relates to adhesive tape fasteners for diapers, diapers attached thereto and methods of use.

The use of adhesive tapes for fastening disposable diapers to secure the diaper around an infant is well known in the art. These adhesive tape fasteners can be in a form ready for use on a diaper, for example mounted on a suitable release liner, or alternatively be attached to a corner of the diaper during manufacture. A pair of such adhesive tape fasteners are normally used to fasten the corners of a diaper. In its simplest form the adhesive tape fastener can be a short length of adhesive tape, one portion of which in use is attached at a marginal portion of the back surface of a diaper to anchor the tape, which leaves the other portion of the tape available for attachment to the marginal portion of the back surface of another part of the diaper to fasten the diaper. However, such adhesive tape fasteners can tear the diaper backing layer during use. U.S. Pat. No. 3,848,598 discloses an improved adhesive tape fastener which has a front surface portion for attachment to the front surface of diaper, a back surface portion for attachment to the back surface of diaper and a fastening portion which can be attached to the back surface of another part of the diaper, which portions are joined and attached at an area of joinder adjacent to the edge of a diaper. U.S. Pat. No. 3,848,598 further discloses that the back surface and fastening portions can be an integral strip and that the fastening portion overlies and is releasably attached to the front surface portion. This type of fastener has two 'anchor' strips which distribute the tensile forces on the diaper surfaces thus reducing the possibility of the anchor strips being pulled out during use. However, these prior art adhesive tape fasteners which have only one fastening tab are not normally capable of being used to refasten the diaper due to the contamination of the adhesive surface of the tab, for example by talc powder and oil, during use. The use of a refastenable adhesive tape fastener is highly desirable as it allows the diaper to be refastened about the infant after it has been inspected or repositioned. U.S. Pat. No. 3,999,546 discloses an adhesive tape fastener, which is attached to a diaper, having two fastening tabs one of which can be separated from the tape after use to allow the second fastening tab to be used to refasten the diaper. The disclosed adhesive tape fastener has two separate fastening tabs which are attached to one surface of an adhesive tape anchoring segment which is folded around the marginal edge portion of the diaper.

It has now been found that a refastenable adhesive tape fastener can be made which employs two tab fasteners and which has the advantage that the adhesive areas of the adhesive tape portions of the fastener in use, are exposed to shear stresses rather than peel stresses.

Accordingly the present invention provides an adhesive tape fastener for a diaper which diaper has a front surface which is adapted to face an infant and a back surface which is opposite the front surface which adhesive tape fastener comprises a first adhesive tape, a second adhesive tape and a third adhesive tape each of which has a back face and a front face which is coated with pressure sensitive adhesive; which first adhesive tape has a free end, a fixed end and a portion between the free end and the fixed end which is adapted for attachment to a marginal portion of the front surface of the diaper to form a first anchor tab, which fixed end is joined to the adhesive face of the second adhesive tape to form a first join; which second adhesive tape has a free end, a fixed end, and a portion between the first join and free end which is adapted to form a first fastening tab for fastening the diaper, which fixed end is joined to the adhesive face of the third adhesive tape to form a second join; which third adhesive tape has a first free end, a second free end, a first portion between the first free end and the second join which is adapted to form a second fastening tab for fastening the diaper and second portion between the second free end and the second join which is adapted for attachment to a marginal portion of the back surface of a diaper to form a second anchor tab; which first fastening tab adhesive face is attached to the back face of the first adhesive tape portion which has a release surface to allow the first fastening tab to be removed therefrom to fasten the diaper; which second fastener tab adhesive face is attached to the back face of the first fastening tab which has a release surface to allow the second fastening tab to be removed therefrom to fasten the diaper which second fastening tab is finger tearable whereby after use it can be detached from the fastener to allow the first fastening tab to be used to refasten the diaper.

The adhesive fastener to the invention can be attached to a diaper. Thus in another aspect the invention provides a diaper which has a front surface which is adapted to face an infant and a back surface which is opposite the front surface and an adhesive tape fastener attached to the diaper which adhesive tape fastener comprises a first adhesive tape, a second adhesive tape and a third adhesive tape each of which has a back face and a front face which is coated with pressure sensitive adhesive; which first adhesive tape has a free end, a fixed end and a portion between the free end and the fixed end which is adapted for attachment to a marginal portion of the front surface of the diaper to form a first anchor tab which fixed end is joined to the adhesive face of the second adhesive tape to form a first join; which second adhesive tape has a free end, a fixed end and a portion between the first join and free end which is adapted to form a first fastening tab for fastening the diaper, which fixed end is joined to the adhesive face of the third adhesive tape to form a second join; which third adhesive tape has a first free end, a second free end, a first portion between the first free end and the second join which is adapted to form a second fastening tab for fastening the diaper and a second portion between the second free end and the second join which is adapted for attachment to a marginal portion of the back surface of a diaper to form a second anchor tab; which first fastening tab adhesive face is attached to the back of the first adhesive tape portion which has a release surface to allow the first fastening tab to be removed therefrom to fasten the diaper; which second fastener tab adhesive face is attached to the back face of the first fastening tab which has a release surface to allow the second fastening tab to be removed therefrom to fasten the diaper, which second fastening tab is finger tearable whereby after use it can be detached from the fastener to allow the first fastening tab to be used to refasten the diaper.

The adhesive tape fastener of the invention will normally be mounted on a release liner to facilitate handling of the fastener and to reduce contamination of its adhesive surfaces. In this form the liner will usually be releasably attached to the adhesive surface of the first adhesive tape and the overlapping portions of the second and third adhesive tapes.

Suitable release liners for the adhesive tape fasteners of the invention can be any of the conventional liners used in the art including silicone release coated papers, polyolefine coated papers and films such as a low density polyethylene, with or without a suitable release coat such as a silicone resin.

The first and second joins can be adjacent to, or spaced apart from each other. However it is preferred that the first and second joins are spaced apart from each other so that the second adhesive tape is provided with a further portion between the first and second joins which is adapted for attachment to an edge of the diaper between its front and back surfaces.

Conveniently the join between the fixed end of the first adhesive tape and the second adhesive tape that is the first join can be made by folding over the fixed end portion of the first adhesive tape so that the adhesive on its front face contacts the adhesive on the front face of the second adhesive tape. The join between the fixed end of the second adhesive tape and the third adhesive tape, that is the second join, can be formed in a similar manner.

Both the first and second fastening tabs can have an uncoated free end, formed for example by folding over the end of the tape, to facilitate peeling the tabs from their underlying release surfaces.

For a similar reason it is preferred that the free end of the release tab projects beyond the free end of the first fastening tab and that the free end of the first fastening tab projects beyond the free end of the second fastening tab.

The dimensions of the individual tape portions can be varied to suit the type of diaper used. An apt adhesive fastening tape which is suitable for use with conventional diapers has a width of 0.75 in. to 1.5 in. for example 1 in., and employs a first adhesive tape with a length of 2.0 in. to 4.0 in. for example, 3.0 in. a second adhesive tape with a length of 1.90 in. to 4.0 in. for example 2.5 in. and a third adhesive tape with a length of 1.5 in. to 4.0 in. for example 2.0 in.

The adhesive tapes used in the invention can be made of a variety of materials normally used in adhesive tapes. The backing material, however, should be flexible, water resistant and have sufficient tensile strength in the length direction to prevent breakage during use. Suitable backings can be made of materials which include plastic films such as polyolefine or polyester films, woven fabrics, non-woven fabrics and strong papers. An apt paper backing has 50 lb to 70 lb. basis weight. (50 lb. to 70./3000 sq. feet).

The backing material used for the third adhesive tape, the first free end portion of which forms the first fastening tab, will be finger tearable. Such a backing material can be provided with a line of weakness but is preferably made of finger tearable material such as paper.

The pressure sensitive adhesive used as a coating on the adhesive tapes can be any of the conventional pressure sensitive adhesives used on industrial or medical tapes providing that the adhesive is water resistant and have sufficient tack and cohesive strength to allow the adhesive fastening tape to be applied and maintained on the diaper in use. Preferably the pressure sensitive adhesive is also non toxic to skin. Suitable pressure sensitive adhesives can be made of wide range of materials including natural and synthetic rubbers, and acrylate ester copolymers.

The release surface on the back face of the adhesive tapes of the fastener can be any of the release coatings normally used on adhesive tapes. A preferred release coat comprises a silicone resin.

The diaper which is attached to the adhesive tape fastener of the invention is preferably a disposable diaper. Such diapers have a front surface, which is adapted to face the infant, and a back surface which is the surface of the diaper opposite the front surface. Conventional disposable diapers usually employ an absorbent layer which is positioned between a liquid permeable front surface sheet and a liquid impermeable back surface sheet which preferably extends around the two long sides of the pad to cover the marginal edges of the liquid permeable sheet. Typical diapers are rectangular in shape and may be box pleated.

Suitable materials for the absorbent layer, the liquid permeable front sheet and the liquid impermeable back sheet are well known in the art. Such materials are disclosed in the hereinbefore mentioned U.S. Pat. No. 3,999,546.

The adhesive tape fastener of the invention can be attached to a marginal portion of the diaper by means of the first and second anchor strips. The diaper will normally have a pair of these adhesive tape fasteners attached to the marginal side portions adjacent to the corners at one end of the diaper.

The two fastening tabs of the attached adhesive fastener can conveniently be maintained in a storage position in which the first fastening tab overlies and is releasably attached to the first anchor tab and the second fastening tab overlies and is releasably attached to the first fastening tab. When required for use to fasten the diaper the individual fastening tabs can be removed from their underlying surfaces by peeling and extended in direction away from the side of the diaper.

The provision of two fastening tabs, one of which can be removed by finger tearing, enables the adhesive tape fastener of the invention to be used to refasten the diaper.

Thus in a further aspect the invention provides a method of refastening a diaper which is attached to an adhesive tape fastener of the invention which comprises detaching a second fastening tab from the fastener by finger tearing and using a first fastening tab to refasten the diaper.

The invention will now be illustrated by reference to the accompanying drawings.

FIG. 1 shows an adhesive tape fastener (1) of the invention mounted on a release liner (2) which comprises a first adhesive tape (3) a second adhesive tape (4) and a third adhesive tape (5) each of which has a front surface coated with pressure sensitive adhesive (6,7,8).

Figure 1:
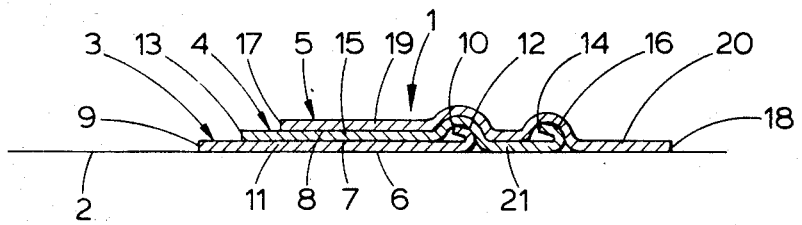
FIG. 1 is a cross section of an adhesive tape fastener of the invention.

The first adhesive tape (3) has a free end (9), a fixed end (10) and a portion (11) between these ends which is adapted for attachment to a marginal portion of the front surface of a diaper to form a first anchor tab. The fixed end (10) is joined to the adhesive face (7) of the second adhesive tape (4) to form a first join (12). The join is formed by contact of the adhesive on a folded over portion of the fixed end (10) with the adhesive on the front face of the second adhesive tape. The second adhesive tape (4) has a free end (13), a fixed end (14) and a portion (15) between the free end (13) and the first join (12) which is adapted for form a first fastening tab for fastening the diaper. The fixed end (14) is joined to the adhesive face (8) of the third adhesive tape (5) to form a second join (16). The second join is formed in a similar manner to that of the first join by contact of the adhesive on a folded over portion of the fixed end (14) with the adhesive on the front face of the second adhesive tape.

As shown in FIG. 1, the second adhesive tape can have a further portion (21) between the first join (12) and the second join (16) which can be adapted for attachment to an edge of a diaper between the front and back surfaces.

The third adhesive tape (5) has a first free end (17), a second free end (18) a first portion (19) between the first free end (17) and the second join (16) which is adapted to form a second fastening tab and a second portion (20) between the second free end (18) and the second join (16) which is adapted for attachment to a marginal portion of the back surface of a diaper to form a second anchor tab. The first fastening tab (15) is attached to the back face of the first adhesive tape portion (11) which has a release surface which is normally a release coating, to allow the fastening tab to be removed by peeling to fasten the diaper. The second fastening tab (19) is attached to the back face of the first fastening tab (15) which has a release surface which is normally a release coating, to allow the fastening tab to be removed by peeling to fasten the diaper. The free end (9) of the first adhesive tape (3) projects beyond the free end (13) of the first fastening tab (15) and similarly the free end (13) of the first fastening tab (15) projects beyond the free end (17) of the second fastening tab (19) to facilitate peeling off the fastening tabs from their underlying release surfaces. The adhesive tape fastener (19) is mounted on a liner (2) which is releasably attached to the adhesive surfaces of the first adhesive tape portion (11) and the overlapping portions (20, 21) of the second and third adhesive tapes.

The second fastening tab (19) is finger tearable so that it can be detached from the fastener to allow the first fastening tab to be used to refasten the diaper.

Figure 2:
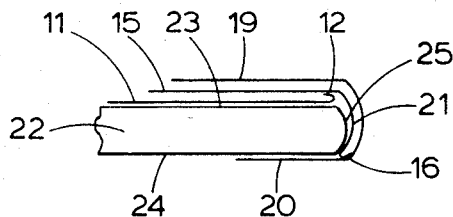
FIG. 2 is a schematic side view of the adhesive tape fastener of FIG. 1 attached to a marginal portion of a diaper showing the fastening tabs in a storage position.

FIG. 2 shows the adhesive tape fastener of FIG. 1 attached to a marginal portion of diaper (22) near a corner which has a front surface (23) adapted to face an infant and a back surface (24) opposite the front surface. In FIG. 2 the first adhesive tape portion (11) is attached to the front surface (23) of the diaper and the second portion (20) of the third adhesive tape is attached to the back surface (24) of the diaper to act as first and second anchor strips respectively. The remaining portion of the second adhesive tape (21) is attached to an edge portion (25) between the front and back surfaces of a diaper. The first (15) and second (19) fastening tabs are shown in a folded position overlying their respective release surfaces.

Figure 3:
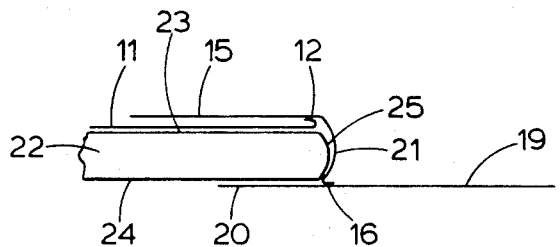
FIG. 3 is a view similar to that of FIG. 2 showing the first fastening tab extended.

In FIG. 3 the second fastening tab (19) is shown in an extended position suitable for fastening the diaper.

Figure 4:
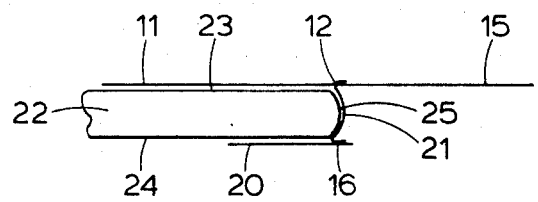
FIG. 4 is a similar view to that of FIG. 3 showing the second fastening tab extended after the first fastening tab has been detached.

In FIG. 4 the first fastening tab (15) is shown in an extended position, after the second fastening tab as been detached from the fastener by finger tearing, so it can be used to refasten the diaper.

The adhesive tape fastener of the invention has the advantage that the adhesive areas of the fastener, for example the first (12) and second (16) joins and the first (11) and second (20) anchor strips, in use are exposed to shear stresses rather than peel stresses.

What is claimed is:

1. In a user-operable, finger-manipulable, adhesive tape-fastener for a disposable sanitary absorbent baby-diaper, which diaper has a front pervious body-contacting surface and also a moisture-impermeable back surface,
   a first adhesive tape, a second adhesive tape, and a third adhesive tape, each of which has a back face and a front face,
   said front faces each being coated with pressure-sensitive adhesive,
   said first adhesive tape having a free end, a fixed end, and a portion between the free end and the fixed end,
   said first adhesive tape adapted for attachment to a marginal portion of the front surface of the diaper to form a first anchor tab,
   said fixed end of the first adhesive tape being joined to the adhesive face of the second adhesive tape to form a first join,
   said second adhesive tape having a free end, a fixed end, and a portion between the first join and free end to form a first fastener tab,
   said fixed end of said second adhesive tape being joined to the adhesive face of the third adhesive tape to form a second join,
   said third adhesive tape having a first free end, a second free end, and a first portion between the first free end and the second join adapted to form a second fastener tab,
   said second adhesive tape having a second portion between the second free end and the second join adapted for user-operable attachment to a marginal portion of the back surface of the diaper to form a second anchor tab,
   said first adhesive tape having a release surface on the back face thereof,
   said fastener tab adhesive tape being removably attached to the release surface of the back face of the first adhesive tape,
   said first fastening tab having a release surface on the back face thereof;
   the adhesive face of the second fastener tab being removably attached to the release surface of the back face of the first fastening tab.

2. The tape-fastener of claim 1, wherein said second fastener tab is finger-tearable so that after user-application to the back surface of the diaper, it can be detached from the fastener to allow the first fastener tab to be used to refasten the diaper.

3. An adhesive tape fastener according to claim 1 in which the first join is formed by contact of the adhesive on a folded over portion of the fixed end of the first adhesive tape with the adhesive on the front face of the second adhesive tape.

4. An adhesive tape fastener according to claim 1 in which the second join is formed by contact of the adhesive on a folded over portion of the fixed end of the second adhesive tape with the adhesive on the front face of the third adhesive tape.

5. An adhesive tape fastener according to claim 1 in which the second adhesive tape has a further portion between the first join and the second join which is adapted for attachment to a marginal edge portion of the diaper between its front and back surfaces.

6. An adhesive tape fastener according to claim 1 in which the free end of the first adhesive tape projects beyond the free end of the first fastening tab.

7. An adhesive tape fastener according to claim 1 in which the free end of the first fastening tab projects beyond the free end of the second fastening tab.

8. A disposable sanitary absorbent baby diaper having a moisture-permeable body-contacting front surface, and also having a moisture-impermeable back surface, said diaper including a user-operable, finger-manipulable adhesive tape-fastener, said fastener comprising a first adhesive tape, a second adhesive tape, and a third adhesive tape, each of which has a back face and a front face, said front faces each being coated with pressure-sensitive adhesive, said first adhesive tape having a free end, a fixed end, and a portion between the free end and the fixed end, said first adhesive tape adapted for attachment to a marginal portion of the front surface of the diaper to form a first anchor tab, said fixed end of the first adhesive tape being joined to the adhesive face of the second adhesive tape to form a first join, said second adhesive tape having a free end, a fixed end, and a portion between the first join and free end to form a first fastener tab, said fixed end of said second adhesive tape being joined to the adhesive face of the third adhesive tape to form a second join, said third adhesive tape having a first free end, a second free end, and a first portion between the first free end and the second join adapted to form a second fastener tab, said second adhesive tape having a second portion between the second free end and the second join adapted for user-operable attachment to a marginal portion of the back surface of the diaper to form a second anchor tab, said first adhesive tape having a release surface on the back face thereof, said fastener tab adhesive tape being removably attached to the release surface of the back face of the first adhesive tape, said first fastening tab having a release surface on the back face thereof;

the adhesive face of the second fastener tab being removably attached to the release surface of the back face of the first fastening tab, said second fastening tab being disposed to operate in alignment with and in shear with the back surface of said diaper and said first fastening tab being disposed in alignment with and to operate in shear with the pervious body-contacting front surface of said diaper.

* * * * *